US010456577B2

(12) United States Patent
Calle et al.

(10) Patent No.: US 10,456,577 B2
(45) Date of Patent: Oct. 29, 2019

(54) AUDITORY PROSTHESIS SYSTEM INCLUDING SOUND PROCESSOR AND WIRELESS MODULE FOR COMMUNICATION WITH AN EXTERNAL COMPUTING DEVICE

(71) Applicant: ADVANCED BIONICS AG, Staefa (CH)

(72) Inventors: Guillermo A. Calle, Moorpark, CA (US); Lakshmi N. Mishra, Valencia, CA (US); Lee F. Hartley, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 383 days.

(21) Appl. No.: 15/122,914

(22) PCT Filed: Mar. 21, 2014

(86) PCT No.: PCT/US2014/031477
§ 371 (c)(1),
(2) Date: Aug. 31, 2016

(87) PCT Pub. No.: WO2015/142355
PCT Pub. Date: Sep. 24, 2015

(65) Prior Publication Data
US 2017/0072195 A1    Mar. 16, 2017

(51) Int. Cl.
*A61N 1/36* (2006.01)
*A61N 1/372* (2006.01)
*H04R 25/00* (2006.01)

(52) U.S. Cl.
CPC ..... *A61N 1/36032* (2013.01); *A61N 1/36036* (2017.08); *A61N 1/37217* (2013.01);
(Continued)

(58) Field of Classification Search
CPC .................................................. A61N 1/37264
See application file for complete search history.

(56) References Cited

U.S. PATENT DOCUMENTS 5,824,022 A * 10/1998 Zilberman ......... A61N 1/36036
607/57
6,731,770 B1    5/2004 Vonlanthen
(Continued)

FOREIGN PATENT DOCUMENTS

EP    1720375    11/2006
EP    2073571    6/2009
(Continued)

OTHER PUBLICATIONS

ReSound LiNX—"Made for iPhone Hearing Aid," http://www.resoundlinx.com/ as accessed Feb. 13, 2014.
(Continued)

*Primary Examiner* — Carl H Layno
*Assistant Examiner* — Jennifer L Ghand
(74) *Attorney, Agent, or Firm* — ALG Intellectual Property, LLC

(57) ABSTRACT

An exemplary auditory prosthesis system includes a sound processor apparatus having 1) an interface assembly that includes at least a first contact that facilitates interchangeable connectivity of a plurality of external components to the sound processor apparatus, the plurality of external components including a programming system, and 2) a control module communicatively coupled to the first contact and that communicates with each of the plurality of external components by way of the first contact. The exemplary auditory prosthesis system may also include a wireless module configured to be interchangeably connected to the interface assembly in place of the programming system, wherein, while the wireless module is interchangeably connected to the interface assembly, the wireless module is
(Continued)

communicatively coupled to the control module by way of the first contact. Corresponding auditory prosthesis systems and methods are also described.

16 Claims, 12 Drawing Sheets

(52) U.S. Cl.
CPC ....... *A61N 1/37264* (2013.01); *H04R 25/554* (2013.01); *H04R 25/556* (2013.01); *H04R 25/602* (2013.01); *H04R 25/606* (2013.01); *H04R 25/70* (2013.01); *H04R 2225/31* (2013.01); *H04R 2225/55* (2013.01)

(56) References Cited

U.S. PATENT DOCUMENTS

| | | | |
|---|---|---|---|
| 7,292,891 B2 | 11/2007 | Hartley | |
| 7,599,500 B1 | 10/2009 | Segel et al. | |
| 8,542,842 B2 | 9/2013 | Zaccaria | |
| 8,554,329 B1 | 10/2013 | Mann et al. | |
| 8,583,244 B1 | 11/2013 | Calle et al. | |
| 2005/0078846 A1* | 4/2005 | Single | A61N 1/08 381/326 |
| 2005/0209657 A1 | 9/2005 | Chung et al. | |
| 2009/0222064 A1* | 9/2009 | Faltys | A61N 1/36036 607/57 |
| 2009/0306743 A1 | 12/2009 | Van Den Heuvel | |
| 2012/0029593 A1* | 2/2012 | Calle | A61N 1/37247 607/57 |
| 2012/0095528 A1 | 4/2012 | Miller, III et al. | |
| 2012/0183165 A1 | 7/2012 | Foo et al. | |
| 2013/0223664 A1 | 8/2013 | Meskens | |
| 2013/0243209 A1 | 9/2013 | Zurbruegg et al. | |
| 2016/0330554 A1* | 11/2016 | Hillbratt | H04R 25/558 |

FOREIGN PATENT DOCUMENTS

| | | |
|---|---|---|
| EP | 2521377 | 11/2012 |
| EP | 2640095 | 9/2013 |
| WO | WO-03/030772 | 4/2003 |
| WO | WO-2005/110530 | 11/2005 |
| WO | WO-2006/023920 | 3/2006 |
| WO | WO-2009/086243 | 7/2009 |
| WO | WO-2010/024856 | 3/2010 |
| WO | WO-2012/106205 | 8/2012 |
| WO | WO-2013/022444 | 2/2013 |

OTHER PUBLICATIONS

Cochlear Nucleus 5, http://www.cochlear.com/wps/wcm/connect/us/recipients/nucleus-5/nucleus-5-lifestyle/how-to-talk-on-the-phone as accessed Apr. 1, 2014.
Partial International Search Report received in International Application No. PCT/US14/031477, dated Oct. 7, 2014.
International Search Report and Written Opinion received in International Application No. PCT/US14/031477, dated Dec. 5, 2014.

* cited by examiner

AUDITORY PROSTHESIS SYSTEM INCLUDING SOUND PROCESSOR AND WIRELESS MODULE FOR COMMUNICATION WITH AN EXTERNAL COMPUTING DEVICE

BACKGROUND INFORMATION

Various types of auditory prosthesis systems have been developed to assist patients who have severe (e.g., complete) hearing loss. For example, cochlear implant systems may provide a sense of hearing for sensorineural hearing loss patients by providing electrical stimulation representative of sound directly to stimulation sites within the cochlea. As another example, electro-acoustic stimulation ("EAS") systems may assist patients with some degree of residual hearing in the low frequencies (e.g., below 1000 Hz) by providing acoustic stimulation representative of low frequency audio content and electrical stimulation representative of high frequency content.

Many auditory prosthesis systems include a sound processor apparatus (e.g., a behind-the-ear ("BTE") sound processing unit, a body worn device, etc.) configured to be located external to the patient. The sound processor apparatus may perform a variety of functions, such as processing audio signals presented to the patient, controlling an operation of one or more implantable devices (e.g., one or more cochlear implants), and providing power to the one or more implantable devices. Various auditory prosthesis systems include interfaces for connecting external components to sound processors using a wired connection. For example, external components, such as a battery or programming system, may be connected to a sound processor via one or more data lines.

Unfortunately, wireless connection of a sound processor apparatus to external devices has been limited. Certain technologies allow for limited wireless communications between a sound processor apparatus and an implanted cochlear implant while the two devices are in close range of each other. However, such wireless technologies do not allow for other types of wireless communication, such as communication between the sound processor apparatus and various commercial accessories, such as mobile computing devices. Conventional technologies that might facilitate such wireless communication with external accessories, such as Bluetooth-based wireless technology, have proven to be impractical to implement in auditory prosthesis systems due to the large size and excessive power consumption of the required components.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
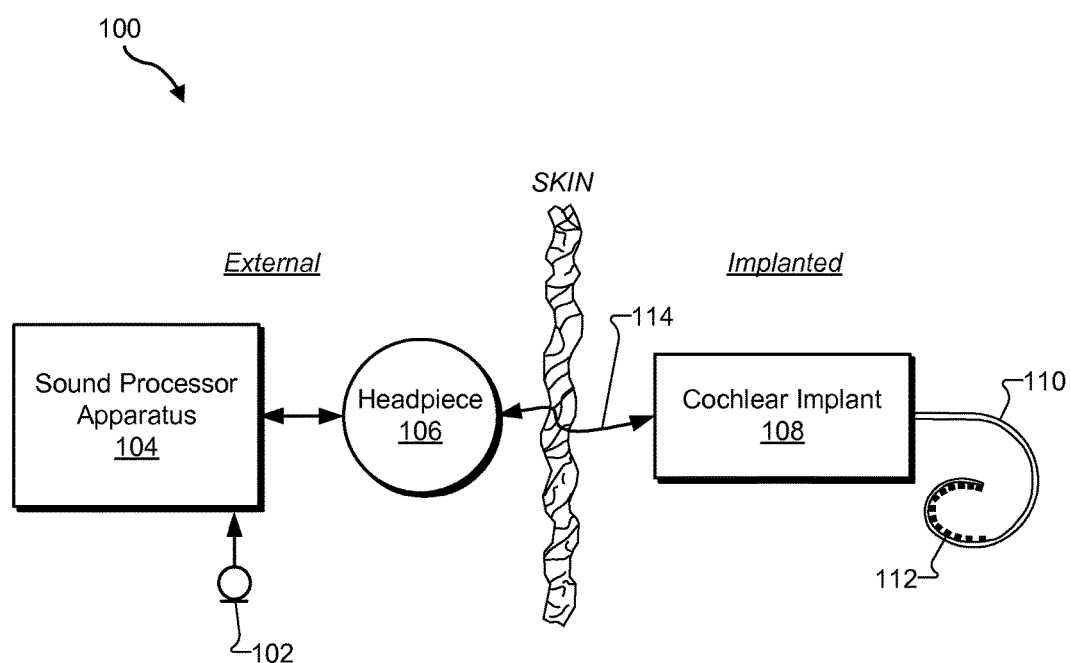
FIG. 1 illustrates an exemplary auditory prosthesis system according to principles described herein.

Auditory prosthesis systems are described herein. As will be described below, an exemplary auditory prosthesis system may include a sound processor apparatus having 1) an interface assembly that includes at least a first contact that facilitates interchangeable connectivity of a plurality of external components to the sound processor apparatus (e.g., by interchangeably connecting to the plurality of external components), the plurality of external components including a programming system, and 2) a control module communicatively coupled to the first contact and that communicates with each of the plurality of external components by way of the first contact. The exemplary auditory prosthesis system may also include a wireless module configured to be interchangeably connected to the interface assembly in place of the programming system, wherein, while the wireless module is interchangeably connected to the interface assembly, the wireless module is communicatively coupled to the control module by way of the first contact.

To illustrate, the sound processor apparatus may be connected to the programming system by way of the interface assembly for purposes of fitting the auditory prosthesis system to a patient. While the programming system is connected to the interface assembly, the control module may use at least the first contact of the interface assembly to communicate with the programming system (e.g., in accordance with a single ended signaling heuristic). Once the fitting is completed, the programming system may be disconnected from the interface assembly and the wireless module may be connected to the sound processor apparatus via the interface assembly. The control module may then use the first contact of the interface assembly to communicate with the wireless module. The wireless module may facilitate communication between the sound processor apparatus and an external wireless device, such as a mobile computing device.

By enabling the wireless module to be connected to the control module of the sound processor apparatus via the same interface assembly as the programming system, various benefits may be realized. For example, the size of the sound processor apparatus may be kept small so as to be practical for everyday use by various patients. Additionally, the wireless module may facilitate wireless communication between an external computing device and the sound processor apparatus. Such wireless communication may facilitate convenient adjustment of various attributes of the sound processor apparatus (e.g., by changing or adjusting a sound processing program executed by the sound processor apparatus or by enabling a telecoil disposed within or otherwise connected to the sound processor apparatus).

Exemplary computing devices that may wirelessly communicate with a sound processor apparatus included in an auditory prosthesis system (e.g., by way of a wireless module interchangeably connected to the sound processor apparatus) are also described herein. In some examples, an external computing device may 1) establish a wireless communication link with a sound processor apparatus associated with a patient (i.e., a sound processor apparatus included in an auditory prosthesis system associated with a patient), 2) receive a first dataset from the sound processor apparatus by way of the wireless communication link, 3) obtain a second dataset from a source other than the sound processor apparatus, and 4) perform a predetermined action with respect to the sound processor apparatus in accordance with the first and second datasets.

As will be described in more detail below, by processing datasets provided by both the sound processor apparatus and a source other than the sound processor apparatus (e.g., the external computing device itself), the external computing device may enhance and/or improve the operation of the sound processor apparatus and thereby provide a relatively better hearing experience for the auditory prosthesis patient.

FIG. 1 illustrates an exemplary auditory prosthesis system 100. As shown, auditory prosthesis system 100 may include various components configured to be located external to a patient including, but not limited to, a microphone 102, a sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor apparatus 104. Additionally or alternatively, microphone 102 may be implemented by one or more microphones disposed within headpiece 106, one or more microphones disposed within sound processor apparatus 104, and/or any other suitable microphone as may serve a particular implementation.

Sound processor apparatus 104 (i.e., one or more components included within sound processor apparatus 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 104 may process the one or more audio signals in accordance with a selected sound processing strategy or program to generate appropriate stimulation parameters for controlling cochlear implant 108. Sound processor apparatus 104 may include or be implemented by a behind-the-ear ("BTE") unit, a body worn device, and/or any other sound processing unit as may serve a particular implementation.

In some examples, sound processor apparatus 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor apparatus 104 and may include an external antenna (e.g., a coil and/or one or more wireless communication components) configured to facilitate selective wireless coupling of sound processor apparatus 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor apparatus 104 (e.g., an audio signal detected by microphone 102) in accordance with one or more stimulation parameters transmitted thereto by sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

The auditory prosthesis system 100 illustrated in FIG. 1 may be referred to as a cochlear implant system because sound processor apparatus 104 is configured to direct cochlear implant 108 to generate and apply electrical stimulation representative of audio content (e.g., one or more audio signals) to one or more stimulation sites within the patient by way of one or more of electrodes 112.

Figure 2:
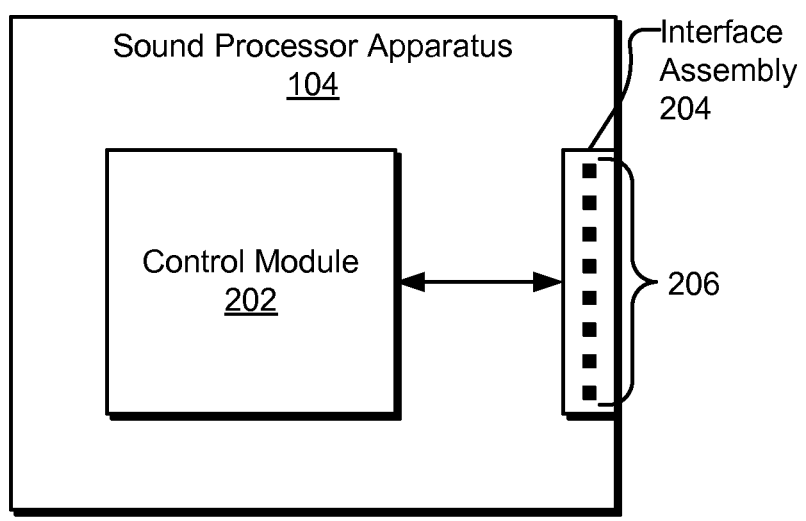
FIG. 2 illustrates exemplary components that may be included within a sound processor apparatus according to principles described herein.

FIG. 2 illustrates exemplary components that may be included within sound processor apparatus 104. As shown, sound processor apparatus 104 may include a control module 202 and an interface assembly 204 (also referred to as a "multipurpose interface assembly") that includes a plurality of contacts 206. It will be recognized that sound processor apparatus 104 may include additional or alternative components as may serve a particular implementation. In some examples, one or more of the components included in sound processor apparatus 104 (e.g., control module 202 and interface assembly 204) may be housed within a single casing.

Control module 202 may be configured to perform one or more operations with respect to one or more components connected to or otherwise communicatively coupled to sound processor apparatus 104. For example, control module 202 may be configured to control an operation of cochlear implant 108, a receiver (i.e., loudspeaker) connected to sound processor apparatus 104, and/or any other device associated with providing electrical and/or acoustic stimulation to a patient. To illustrate, control module 202 may process an audio signal presented to the patient, generate one or more stimulation parameters based on the processing of the audio signal, and direct cochlear implant 108 to generate and apply electrical stimulation representative of the audio signal to the patient in accordance with the stimulation parameters (e.g., by transmitting the stimulation parameters to cochlear implant 108).

Control module 202 may be additionally or alternatively configured to interact with one or more external components connected to sound processor apparatus 104 by way of interface assembly 204. To this end, control module 202 may overload at least some of contacts 206 with a plurality of functions. Exemplary manners in which this may be performed will be described below.

Control module 202 may be implemented by any suitable combination of integrated circuits, circuitry, processors, and/or computing devices configured to perform one or more of the operations and/or functions described herein. Exemplary implementations of control module 202 will be described below.

Interface assembly 204 may be configured to facilitate interchangeable connectivity of a plurality of external components to sound processor apparatus 104. To this end, interface assembly 204 may include a plurality of contacts 206. The number of contacts 206 may vary as may serve a particular implementation. For example, in some implementations, interface assembly 204 may include no more than eight contacts 206.

Each contact 206 may include any type of conductive contact (e.g., a male contact such as a pin or a female contact such as a receptacle) as may serve a particular implementation. Each contact 206 may be configured to be electrically coupled to a corresponding contact included in an interface assembly associated with (e.g., integrated into and/or otherwise coupled to) an external component while the external component is connected to interface assembly 204.

Figure 3:
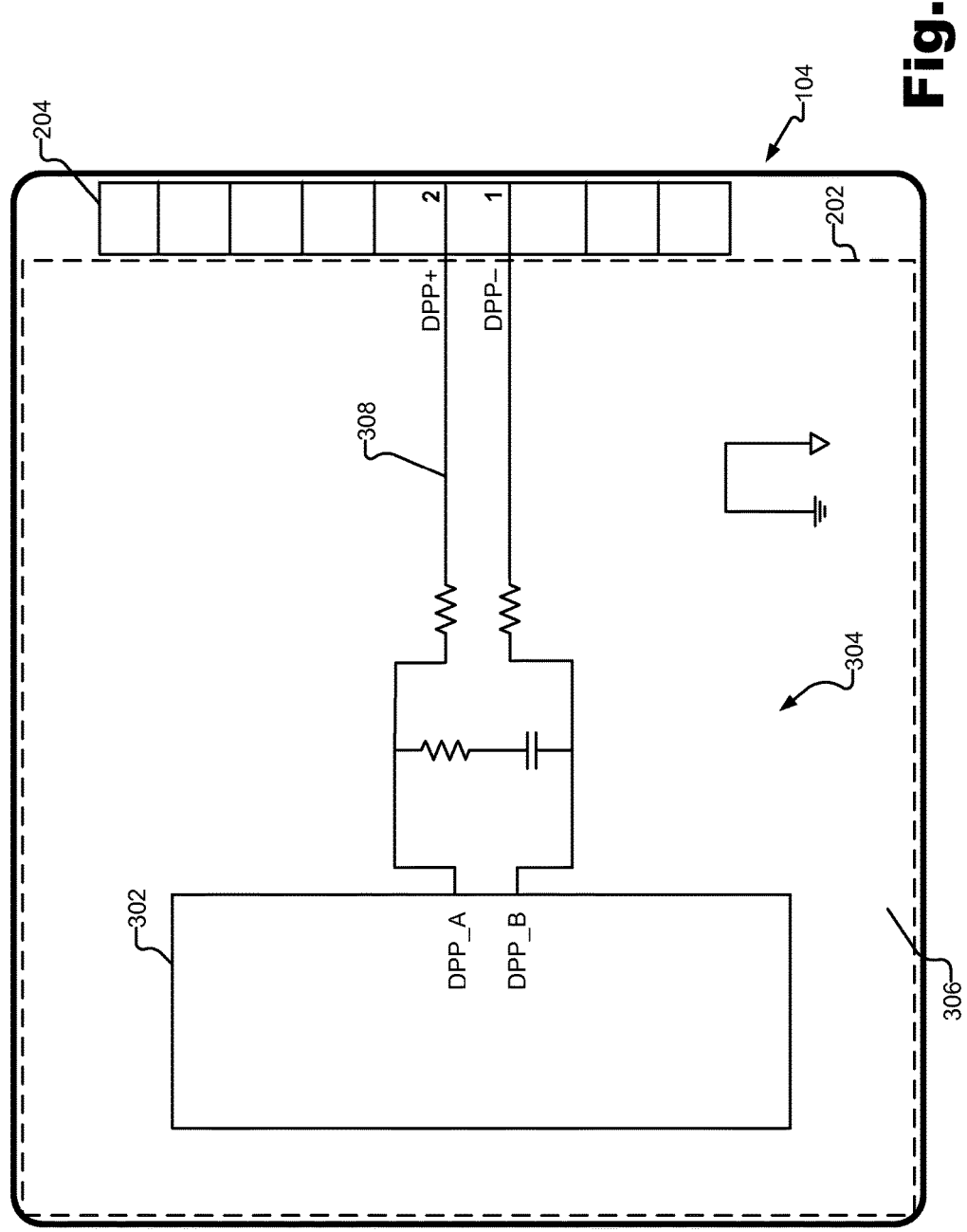
FIG. 3 shows an exemplary configuration of the sound processor apparatus of FIG. 2 according to principles described herein.

Control module 202 and interface assembly 204 may be implemented in any suitable manner. For example, FIG. 3 shows an exemplary configuration of sound processor apparatus 104 wherein control module 202 is implemented by an integrated circuit ("IC") 302 and various on-board electrical components 304 (e.g., resistors, capacitors, and grounds— the value of which may be selected as may best serve a particular implementation) disposed on a printed circuit board 306.

IC 302 may be implemented by any suitable combination of integrated circuits as may serve a particular implementation. IC 302 may include a plurality of ports. For example, as shown in FIG. 3, IC 302 may include differential signaling ports (DPP_A and DPP_B). Additional or alternative ports may be included in IC 302 as may serve a particular implementation.

In this particular implementation, interface assembly 204 has eight contacts, each of which may be connected to IC 302 and/or one or more electrical components 304 by way of one or more data lines (e.g., data line 308). The illustrated contacts connected to the differential signaling ports (DPP_A and DPP_B) are labeled 1 and 2 and named DPP− and DPP+, respectively.

Figure 4:
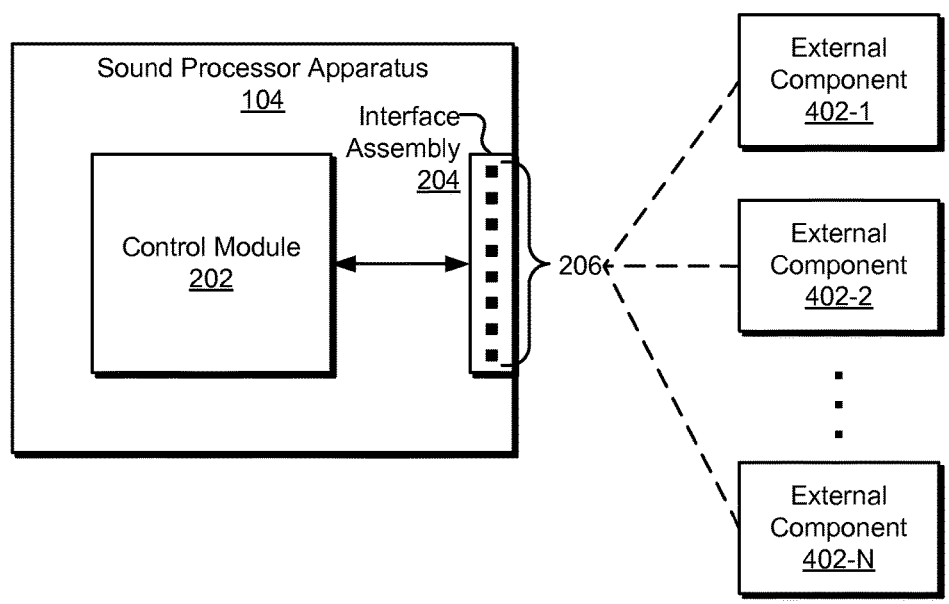
FIG. 4 shows that multiple external components may be interchangeably connected to an interface assembly of a sound processor apparatus according to principles described herein.

FIG. 4 shows that multiple external components 402 (e.g., external components 402-1 through 402-N) may be interchangeably connected to interface assembly 404 of sound processor apparatus 104 by way of contacts 206. Exemplary external components 402 include, but are not limited to, a wireless module, various types of battery modules (e.g., a rechargeable battery module such as a Li-Ion battery module, a non-rechargeable battery module such as a Zn-Air battery module, an audio-enabled battery module (e.g., a battery module that has an audio receiver connected thereto), etc.), a programming system (e.g., a fitting device), a listening check interposer, an audio receiver (e.g., a digital modulation ("DM") receiver), an off-ear power module, and/or any other type of external component as may serve a particular implementation.

In some examples, only a single external component 402 may be connected to sound processor apparatus 104 by way of interface assembly 204 at any given time. In other examples, multiple external components 402 may be concurrently connected to sound processor apparatus 104 by way of interface assembly 204. For example, a listening check interposer may be connected directly to interface assembly 204 and a battery module may be connected to the listening check interposer.

FIGS. 5-10 illustrate various external components 402 that may be interchangeably connected to sound processor apparatus 104 by way of interface assembly 204, as well as configurations of auditory prosthesis systems including the various external components 402. It will be recognized that the external components and system configurations described in connection with FIGS. 5-10 are merely illustrative of the many different external components and system configurations that may be connected to sound processor apparatus 104 by way of interface assembly 204 in accordance with the systems and methods described herein. The external components 402 described in connection with FIGS. 5-10 may each be interchangeably connected to the interface assembly 204 illustrated in FIG. 4.

Figure 5:
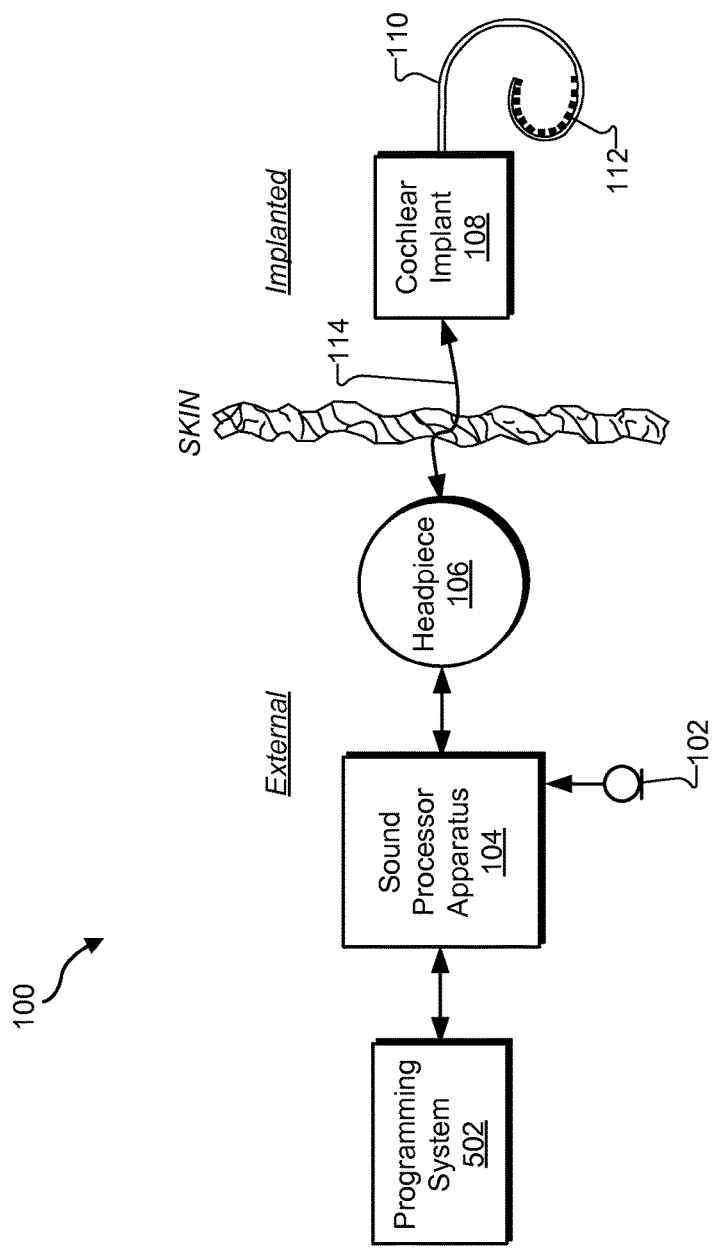
FIG. 5 illustrates an exemplary auditory prosthesis system including a programming system interchangeably connected to a sound processor apparatus according to principles described herein.

FIG. 5 illustrates an implementation of auditory prosthesis system 100 in which a programming system 502 is connected to sound processor apparatus 104. In this configuration, programming system 502 may be interchangeably connected to interface assembly 204 illustrated in FIG. 4. Programming system 502 may be configured to communicate with (e.g., provide programming data to) sound processor apparatus 104 (i.e., control module 202), provide power to sound processor apparatus 104, and/or otherwise interact with sound processor apparatus 104 while programming system 502 is connected to sound processor apparatus 104.

Figure 6:
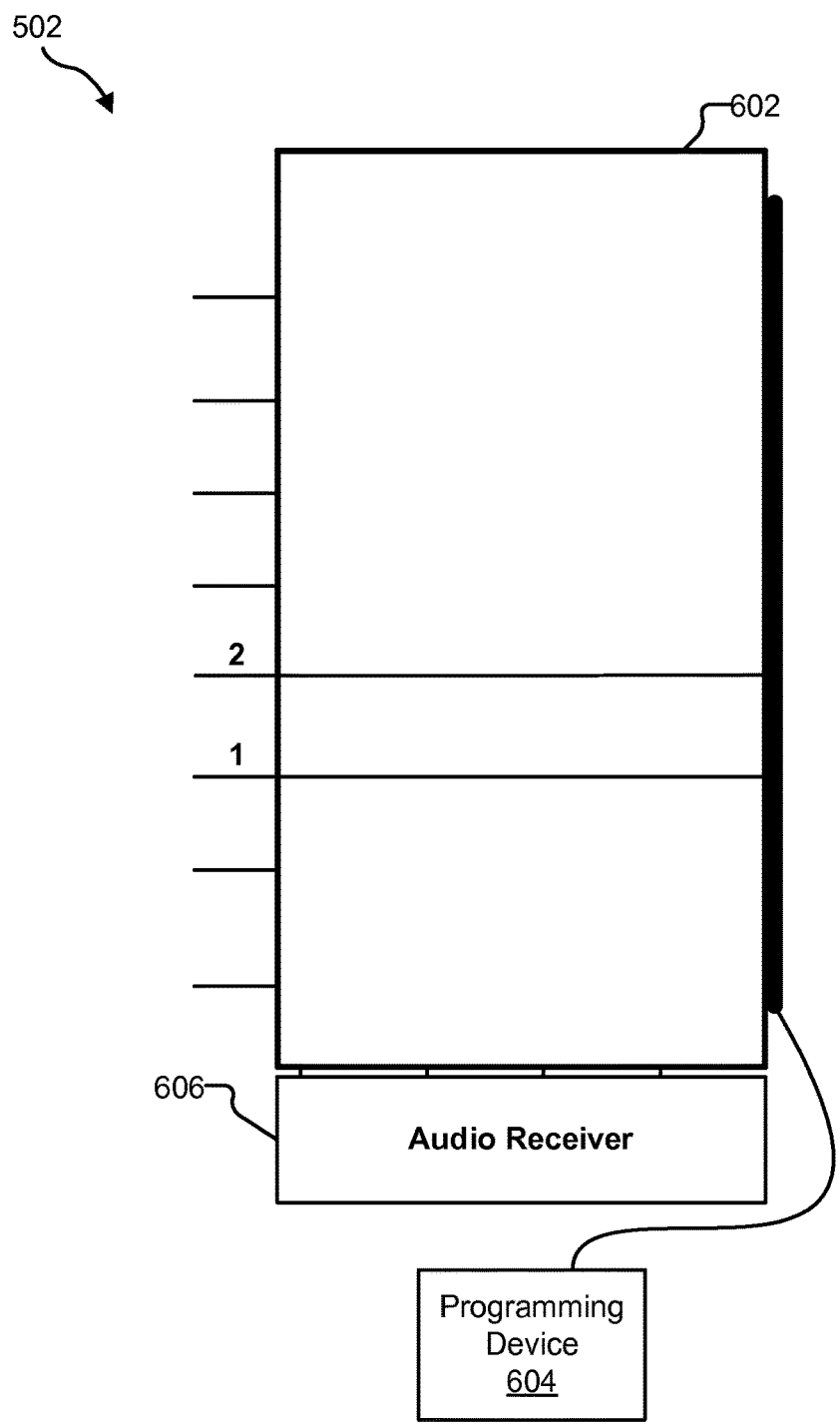
FIG. 6 illustrates a programming system that may be interchangeably connected to an interface assembly of a sound processor apparatus according to principles described herein.

FIG. 6 illustrates an exemplary programming system 502. As shown, programming system 502 may include a connection interface 602 coupled to a programming device 604. Programming device 604 may include, but is not limited to, a fitting station, a personal computer, a laptop computer, a handheld device, a mobile device (e.g., a mobile phone), a clinician's programming interface ("CPI") device, and/or any other suitable device used to program sound processor apparatus 104 as may serve a particular implementation. Programming device 604 may be configured to communicate with (e.g., provide programming data to) sound processor apparatus 104 (i.e., control module 202), provide power to sound processor apparatus 104, and/or otherwise interact with sound processor apparatus 104 while programming system 502 is connected to interface assembly 204.

Connection interface 602 may be implemented, for example, by a programming cable, and may include eight contacts configured to be in communication with (i.e., make physical contact with) corresponding contacts 206 included in interface assembly 204 while programming system 502 is connected to interface assembly 204. Two of the contacts of connection interface 602 (labeled 1 and 2) may correspond to two contacts 206 (e.g., contacts labeled 1 and 2 in FIG. 3) included in interface assembly 204.

As shown, an audio receiver 606 (e.g., an FM or DM receiver) may be coupled to connection interface 602 and configured to provide audio to sound processor apparatus 104 while programming system 502 is connected to interface assembly 204.

Figure 7:
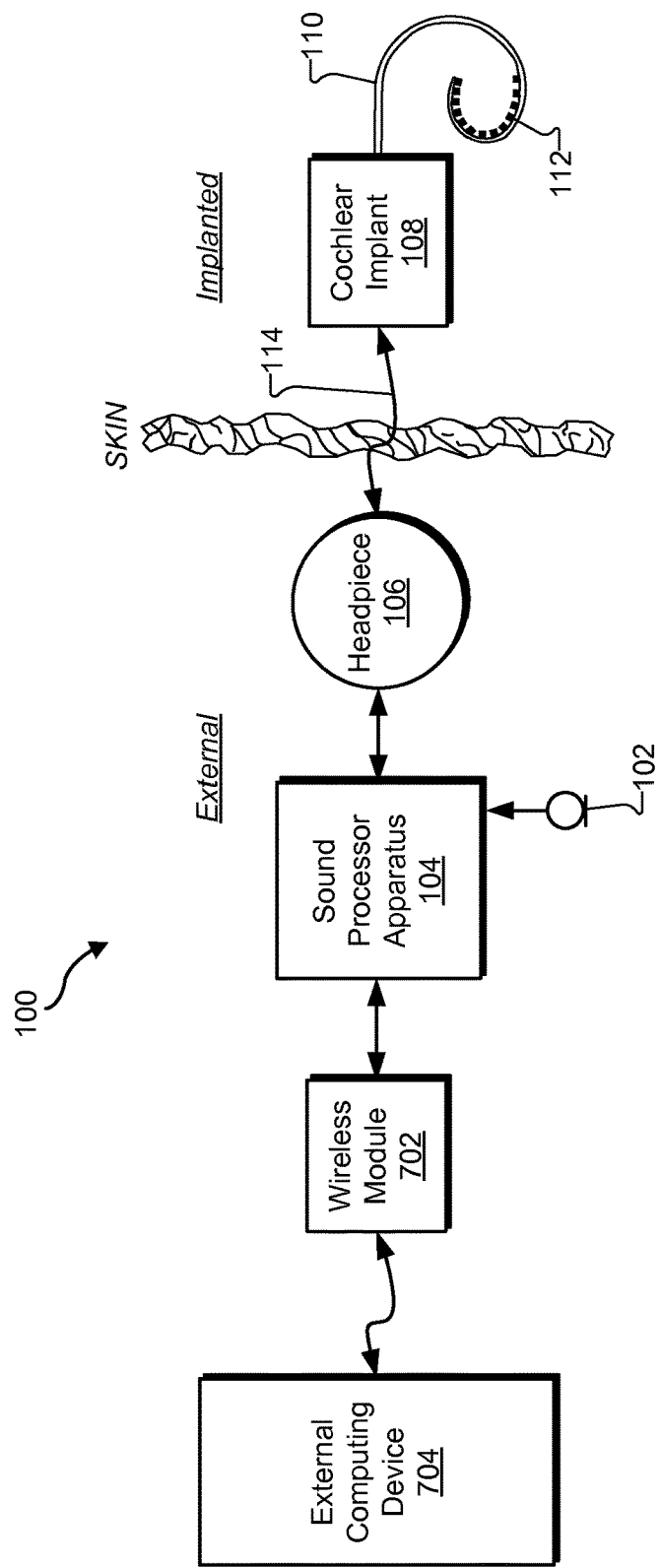
FIG. 7 illustrates an exemplary auditory prosthesis system including a wireless module interchangeably connected to a sound processor apparatus according to principles described herein.

FIG. 7 illustrates another implementation of auditory prosthesis system 100 in which a wireless module 702 is connected to sound processor apparatus 104 and is in wireless communication with an external computing device 704. In this configuration, wireless module 702 may be interchangeably connected to interface assembly 204 illustrated in FIG. 4. Wireless module 702 may include, for example, a Bluetooth device and/or any other suitable device configured to send and receive communication signals wirelessly as may serve a particular implementation. Wireless module 702 may be configured to communicate with sound processor apparatus 104 (i.e., control module 202), wirelessly communicate with one or more external, wireless-enabled devices (e.g., external computing device 704), and/or otherwise interact with sound processor apparatus 104 while wireless module 702 is connected to interface assembly 204.

Figure 8:
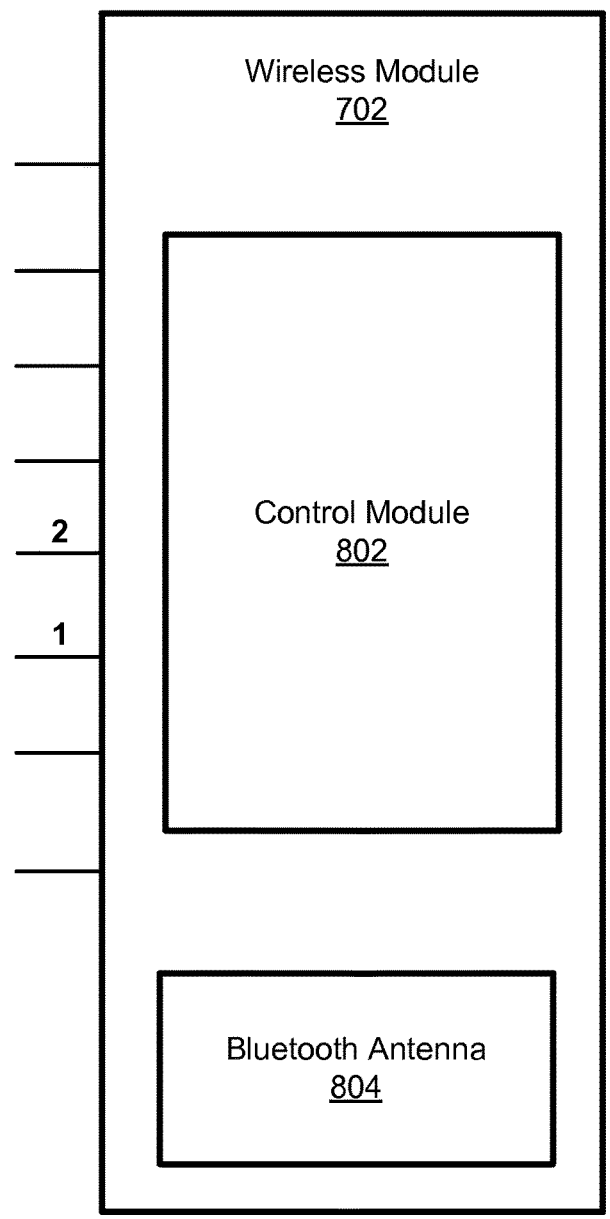
FIG. 8 illustrates a wireless module that may be interchangeably connected to an interface assembly of a sound processor apparatus according to principles described herein.
Figure 9:
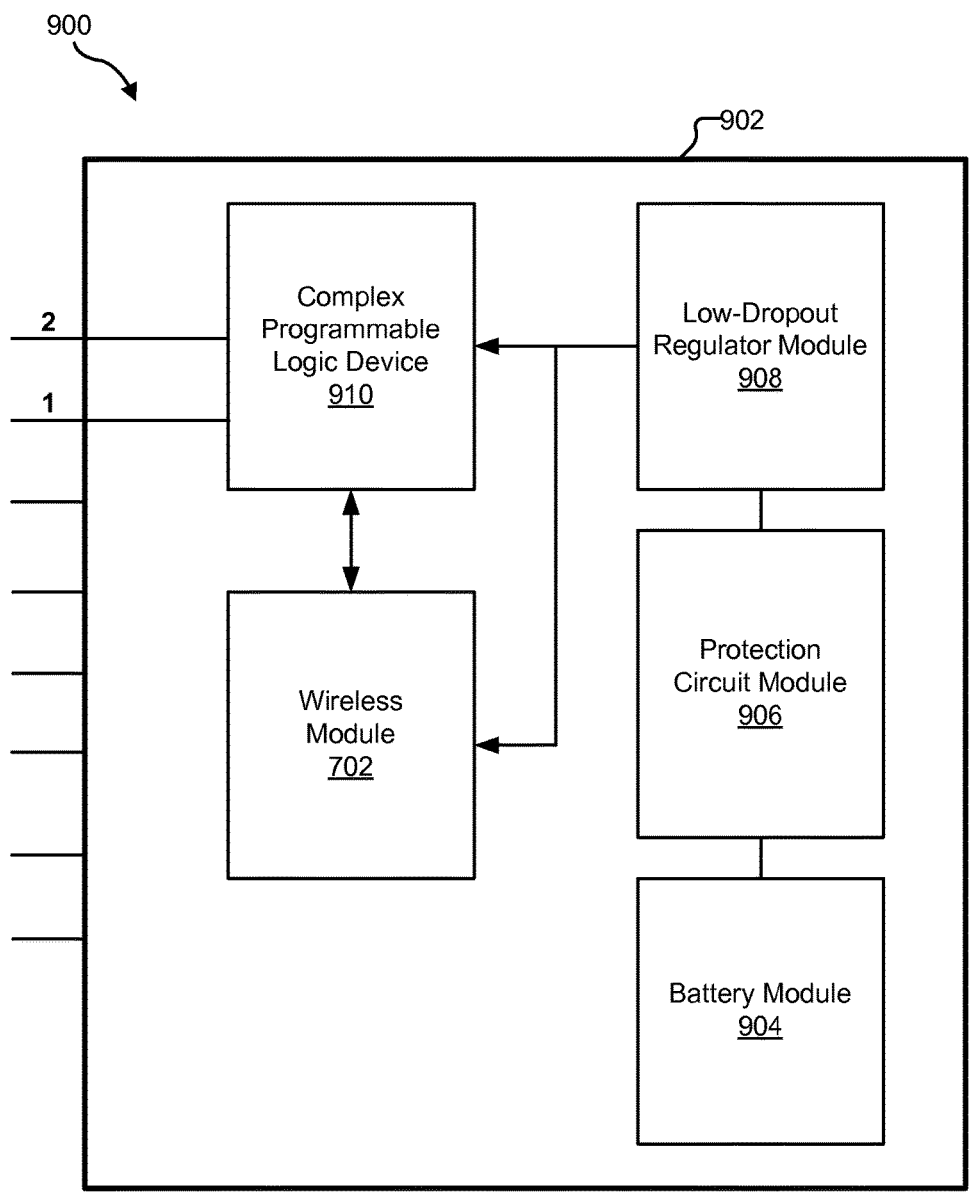
FIG. 9 shows a battery assembly that includes various components, including a wireless module and a battery module, that may be interchangeably connected to an interface assembly of a sound processor apparatus according to principles described herein.

FIG. 8 illustrates an exemplary wireless module 702. As shown, wireless module 702 may include eight contacts configured to be in communication with (i.e., make physical contact with) corresponding contacts 206 included in interface assembly 204 while wireless module 702 is connected to interface assembly 204. It will be recognized that while eight contacts are shown in FIG. 9, wireless module 702 may include any number of contacts as may serve a particular implementation. Two of the contacts of wireless module 702 (labeled 1 and 2) may correspond to two contacts 206 (e.g., contacts labeled 1 and 2 in FIG. 3) included in interface assembly 204.

In some examples, as illustrated above in connection with FIG. 3, contacts 1 and 2 of interface assembly 204 are connected to output ports of IC 302 labeled DPP_B and DPP_A, respectively. A differential driver (not shown) included within IC 302 may be connected to these output ports and configured to use the ports to output differential signals used to communicate with wireless module 702 while wireless module 702 is connected to interface assembly 204. It will be recognized that any other number of contacts (e.g., one contact) may be used by IC 302 to communicate with wireless module 702 in any suitable manner (e.g., by using communication schemes other than differential signaling) as may serve a particular implantation.

Wireless module 702 may include a control module 802 (i.e., a microcontroller) and a Bluetooth antenna 804. Control module 802 may interface with control module 202 of sound processor apparatus 104 and may be configured to control an operation of Bluetooth antenna 804 in accordance with differential signals and/or other signals received from sound processor apparatus 104. Bluetooth antenna 804 may be configured to facilitate selective wireless coupling of wireless module 702 to one or more external wireless-enabled devices.

In some examples, wireless module 702 may be configured to operate in accordance with a Bluetooth Low Energy standard (e.g., Bluetooth LE, Bluetooth BLE, Bluetooth Smart, or Bluetooth 4.0). As such, wireless module 702 may be reduced in size and may use less power than conventional Bluetooth technologies. For example, wireless module 702 may have a maximum current consumption of approximately 10 mA during operation and a maximum power consumption of approximately 50 mW during operation. In some examples, wireless module 702 may have a current consumption of approximately 7 mA or less during operation and a power consumption of approximately 40 mW or less during operation. To illustrate, wireless module 702 may consume approximately 5 mA and approximately 36 mW during operation. Wireless module 702 may include a sleep mode, during which current consumption is as low as 600 nA. Additionally, wireless module 702 may occupy a maximum area of approximately 70 mm$^2$. For example, wireless module 702 may occupy an area of approximately 60 mm$^2$ or less. To illustrate, wireless module 702 may occupy an area of approximately 56 mm$^2$. It will be recognized that the technical specifications of wireless module 702 described herein are merely exemplary. Wireless module 702 may be of any suitable size and may consume any suitable amount of current and/or power as may serve a particular implementation.

Wireless module 702 may be connected to a battery that powers wireless module 702. A battery module connected to wireless module 702 may also be utilized to power sound processor apparatus 104. In some examples, wireless module 702 may be disposed in the same housing as the battery module and/or one or more other external components. For example, as shown in FIG. 9, a battery assembly 900 may include a housing 902 that houses both wireless module 702 and a battery module 904. In some alternative examples, battery assembly 900 may include wireless module 702 in a separate housing than battery module 904. Battery assembly 900 may include any number of contacts (e.g., eight contacts) configured to be in communication with (i.e., make physical contact with) corresponding contacts 206 included in interface assembly 204 while wireless module 702 is connected to interface assembly 204. Two of the contacts of wireless module 702 (labeled 1 and 2) may correspond to two contacts 206 (e.g., contacts labeled 1 and 2 in FIG. 3) included in interface assembly 204.

Battery module 904 may include any suitable type of battery, including, for example, a rechargeable battery module such as a Li-Ion battery module and/or a non-rechargeable battery module such as a Zn-Air battery module. In some examples, battery assembly 900 may be configured as an audio-enabled battery module (e.g., a battery module that has an audio receiver connected thereto) that utilizes battery module 904 in response to the detection of environmental noise exceeding a specified decibel level.

A battery module 904 that is a Li-Ion battery module may include a rechargeable power supply module configured to provide power to wireless module 702 and sound processor apparatus 104. An exemplary voltage range for the power provided by the power supply module is up to 4.2 volts DC ("VDC").

A battery module 904 that is a Zn-Air battery module may include a non-rechargeable power supply module (e.g., a battery pack that includes one or more Zn-Air batteries) configured to provide power to wireless module 702 and sound processor apparatus 104. An exemplary voltage range for the power provided by the power supply is up to 1.6 VDC per cell (e.g., 3.2 VDC in cases where the Zn-Air battery module includes two cells).

Battery assembly 900 may include a protection circuit module 906 having a printed circuit board assembly that is configured to prevent battery module 904 (e.g., Li-Ion rechargeable battery module) from over charging or over dis-charging. Battery assembly 900 may further include a low-dropout regulator module 908 to linearly regulate voltage output while minimizing power dissipation and reducing heat generation. Voltage may be supplied from low-dropout regulator module 908 to wireless module 702 and a complex programmable logic device ("CPLD") 910 of battery assembly 900. In some examples, CPLD 910, or alternatively, a microcontroller, may provide a programmable interface between wireless module 702 and sound processor apparatus 104.

Battery assembly 900 may have an overall maximum power consumption of approximately 70 mW during operation. In some examples, battery assembly 900 may have a power consumption of approximately 60 mW or less during operation. To illustrate, an exemplary battery assembly 900 may consume approximately 50 mW during operation and may have a battery life of approximately 18 hours when a battery module 904 comprising a Li-Ion rechargeable battery module (230 mAh battery module having an average voltage output of 2.8 V) is utilized.

In some examples, battery assembly 900 may maintain a data log that keeps track of various characteristics related to battery assembly 900, such as an amount of memory (e.g., RAM) utilized by battery assembly 900 or a remaining amount of battery life for battery module 904. Such data logs may be accessible for monitoring or troubleshooting of battery assembly 900 by an external computing device (e.g., external computing device 704).

Figure 10:
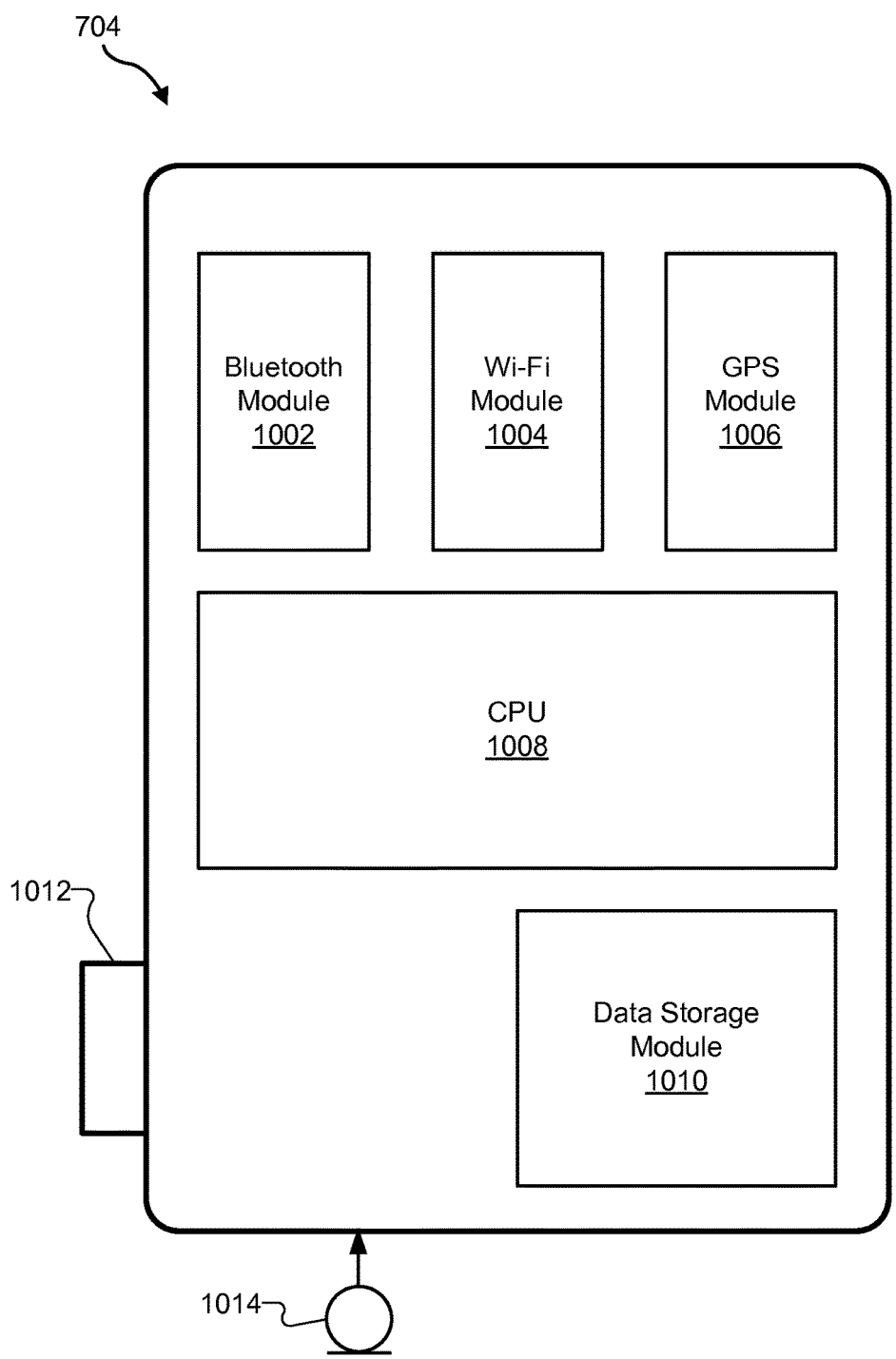
FIG. 10 shows an external computing device that may be wirelessly connected to sound processor apparatus by way of wireless module according to principles described herein.

FIG. 10 shows an external computing device 704 that may be wirelessly connected to sound processor apparatus 104 by way of wireless module 702. External computing device 704 may represent any type or form of computing device, such as a mobile-communication device, including, without limitation, a cellular phone, a smart phone, a tablet computer, a laptop computer, a personal digital assistant device ("FDA"), a GPS receiver, combinations of one or more of the same, or any other suitable wireless-enabled computing device as may serve a particular implementation. For example, external computing device 704 may comprise a mobile computing device (e.g., cell phone or a tablet computer) that is utilized by a patient. In some examples, external computing device 704 may alternatively or additionally represent a desktop device, a multimedia player, a game console, an embedded system, combinations of one or more of the same or any other suitable computing device as may serve a particular implementation.

External computing device 704 may include at least one wireless communication module capable of establishing a wireless connection with wireless module 702 and/or one or more other wireless communication or transmitting devices. As illustrated in FIG. 10, external computing device 704 may include a Bluetooth module 1002 (e.g., a module compatible with a Bluetooth Low Energy standard), a Wi-Fi module 1004, a GPS module 1006, combinations of one or more of the same, and/or any other suitable wireless module as may serve a particular implementation. In some examples, external computing device 704 may be configured to communicate over a cellular device network using a cellular radio frequency signal. External computing device 704 may be configured to communicate with (e.g., provide programming data to and/or receive data from) sound processor apparatus 104 (i.e., control module 202) when external computing device 704 is wirelessly connected to wireless module 702.

External computing device 704 may also include a central processing unit ("CPU") 1008 and a data storage module 1010. CPU 1008 may include one or more processors capable of receiving and processing data or interpreting and executing computer-readable instructions. Data storage module 1010 may generally represent any type or form of storage device or medium capable of storing data and/or other computer-readable instructions. For example, data storage module 1010 may be a magnetic disk drive (e.g., a so-called hard drive), an optical disk drive, a flash drive, combinations of one or more of the same, or any other suitable non-transitory storage medium as may serve a particular implementation.

External computing device 704 may also be configured to communicate wirelessly with devices other than wireless module 702 and sound processor apparatus 104. For example, external computing device 704 may wirelessly send data to and/or receive data from one or more other sources, including, for example, other external computing devices, via any suitable type of wireless communication signal, without limitation. In some examples, external computing device 704 may be configured to communicate with at least one other external device using a wired connection via a suitable communication interface 1012.

Communication interface 1012 may represent any type or form of communication device or adapter capable of facilitating communication between external computing device 704 and one or more additional devices or networks. Examples of communication interface 1012 include, without limitation, a wired network interface (such as a network interface card), a wireless network interface (such as a wireless network interface card), a modem, and any other suitable interface. Communication interface 1012 may additionally represent a host adapter configured to facilitate communication between external computing device 704 and one or more additional network or storage devices via an external bus or communications channel, including, without limitation, SCSI host adapters, USB host adapters, IEEE 694 host adapters, SATA and eSATA host adapters, ATA and PATA host adapters, Fibre Channel interface adapters, Ethernet adapters, or any other suitable adapter as may serve a particular implementation.

In some examples external computing device 704 may be configured to receive and utilize data received wirelessly from sound processor apparatus 104 via wireless module 702. For example, external computing device 704 may receive a dataset (referred to herein as a first dataset) from sound processor apparatus 104. The dataset may be representative of any suitable information. For example, the dataset may be representative of one or more sound processing programs loaded onto and/or executable by sound processor apparatus 104. In this scenario, the dataset received from sound processor apparatus 104 may be utilized by external computing device 704 to determine a suitable sound processing program to be executed by sound processor apparatus 104. Additionally or alternatively, a dataset received by external computing device 704 from sound processor apparatus 104 may, for example, indicate measurements, such as diagnostic measurements (e.g., impedance measurements, neural response imaging measurements, and/or conditioning measurements), obtained by sound processor apparatus 104 from cochlear implant 108 implanted within a patient. The dataset may additionally or alternatively provide an indication of one or more user preferences associated with a patient utilizing auditory prosthesis system 100.

In some examples, data from a source other than auditory prosthesis system 100 (referred to herein as a second dataset) may also be utilized by external computing device 704 in conjunction with data obtained from auditory prosthesis system 100 (i.e., the first dataset) to perform a predetermined action with respect to the sound processor apparatus. The second dataset may be acquired by external computing device 704 in any suitable manner. For example, external computing device 704 itself may acquire or generate the second dataset. To illustrate, external computing device 704 may obtain the second dataset by taking one or more measurements of an area surrounding external computing device 704. In some embodiments, external computing device 704 may also include at least one measurement tool, such as a microphone 1014. Microphone 1014 may be configured to detect audio signals at a location of external computing device 704 (i.e., environmental audio signals). Such audio signals may be used to determine a sound level and/or an audio profile (i.e., environmental audio profile) in the vicinity of external computing device 704, which may be useful in determining a suitable sound processing program for use by sound processor apparatus 104.

The second dataset may additionally or alternatively be obtained from one or more other computing devices that are in communication with external computing device 704. For example, data received by external computing device 704 from other computing devices may include data indicating a physical location (e.g., GPS coordinates) of external computing device 704. Such physical location data may alternatively be acquired by the external computing device 704 itself, depending on the capabilities of the external computing device 704). Additionally or alternatively, data received by external computing device 704 from other computing devices may identify a sound level and/or audio profile in the vicinity of external computing device 704.

As mentioned, external computing device 704 (e.g., CPU 1008) may perform a predetermined action in accordance with the first and second datasets. In some examples, user profile data that is specific to a user of sound processor apparatus 104 may also be utilized in conjunction with the first and second datasets in performing the predetermined action.

A predetermined action performed by external computing device 704 may include directing sound processor apparatus 104 to change at least one of a sound processing program executed by the sound processor apparatus 104 and a sound processing parameter utilized by sound processor apparatus 104. For example, external computing device 704 may receive a first dataset from sound processor apparatus 104 that identifies various executable sound processing programs loaded onto sound processor apparatus 104. External computing device 704 may additionally receive or generate a second dataset that indicates that the patient is located in a noisy environment (e.g., a crowded restaurant). Based on the first and second datasets, external computing device 704 may identify one of the sound processing programs loaded onto sound processor apparatus 104 that that is suitable for such an environment (e.g., a sound processing program configured to apply a noise reduction heuristic to audio content presented to the auditory prosthesis patient) and direct sound processor apparatus 104 to switch to and begin operating in accordance with the identified sound processing program.

As another example, external computing device 704 may receive a first dataset from sound processor apparatus 104 that identifies a particular sound processing program currently being executed by sound processor apparatus 104. External computing device 704 may additionally receive or generate a second dataset that indicates that the patient is located in a noisy environment, as described above. Based on the first and second datasets, external computing device 704 may adjust a sound processing parameter (e.g., a noise canceling parameter) associated with the sound processing program being executed by sound processor apparatus 104.

Performing the predetermined action may additionally or alternatively include identifying a sound processing program that is not already loaded onto sound processor apparatus 104, and then transmitting data representative of the sound processing program from external computing device 704 to sound processor apparatus 104. For example, external computing device 704 may, based on location data detected by external computing device 704, identify a particular sound processing program that would be ideal for the location indicated by the location data. External computing device 704 may also receive a dataset from sound processor apparatus 104 that indicates that the particular sound processing program is not already loaded onto sound processor apparatus 104. In response, external computing device 704 may transmit data representative of the particular sound processing program to sound processor apparatus 104 so that the sound processor apparatus 104 may operate in accordance with the particular sound processing program.

As another example, external computing device 704 may determine, in response to an audio analysis of a particular location, that sound processor apparatus 104 should utilize a particular microphone, sound processing, and/or front end processing heuristic. To illustrate, GPS may be utilized by external computing device 704 to determine that a user of auditory prosthesis system 100 is driving in a vehicle. In response to this determination, external computing device 704 may recommend or direct sound processor apparatus 104 to operate in accordance with a particular sound processing program.

In some examples, a predetermined action performed by external computing device 704 may include enabling or disabling a functionality of auditory prosthesis system 100. For example, a telecoil functionality of sound processor apparatus 104 may be enabled or disabled based on auditory prosthesis system 100 being located within an area having a telecoil loop. To illustrate, the auditory prosthesis patient may enter an area (e.g., an auditorium) that has a telecoil loop. External computing device 704 may be configured to automatically direct control module 202 of sound processor 104 to enable and/or disable telecoil functionality or to change a program executed by sound processor apparatus 104 in conjunction with a telecoil. For example, a telecoil of sound processor apparatus 104 may be enabled or disabled based on auditory prosthesis system 100 being located within an area having a telecoil loop.

Detection of a telecoil loop may be determined by external computing device 704 through, for example, GPS positioning and/or through a wireless notification when a user enters or leaves a telecoil loop. For example, external computing device 704 may detect the location of the patient (e.g., by detecting GPS coordinates of the patient) and use the detected location to search a database (e.g., a web-based database and/or a database maintained within data storage module 1010) for an area that has a telecoil loop. If the database indicates that the detected location is within a vicinity of a telecoil loop, (and if the sound processor apparatus 104 has provided data to external computing device 704 indicating that a telecoil is included in sound processor apparatus 104), external computing device 704 may automatically enable the telecoil included within sound processor apparatus 104 and/or notify the patient that he or she may manually enable the telecoil.

In some examples, a telecoil of sound processor apparatus 104 may be enabled or disabled based on a telephone device status. For example, a telephone device that is configured to communicate wirelessly with a telecoil may receive an incoming call, at which point external computing device 704 may direct sound processor apparatus 104 to enable the telecoil so as to enable the call signal to be transmitted directly from the telephone device to the telecoil. Once such a telephone call is completed, external computing device 704 may direct sound processor apparatus 104 to disable the telecoil.

In some examples, a predetermined action performed by external computing device 704 may include enabling or disabling one or more functionalities of auditory prosthesis system 100 during certain specified time periods. For example, external computing device 704 may detect a certain time period in which the patient desires to disable the sound processor apparatus 104 (e.g., a time period associated with a religious holiday, such as Shabbat. In response, external computing device 704 may disable one or more functions of auditory prosthesis system 100.

In some examples, external computing device 704 may be utilized as a remote control device that allows a user to adjust, via wireless module 702, one or more parameters of a sound processing program that is executed by sound processor apparatus 104. For example, external computing device 704 may run an application that enables external computing device 704 to remotely monitor and/or control various functions of sound processor apparatus 104, including, without limitation, controlling system volume, sensitivity, battery status, and lock status. In some examples, external computing device 704 may run an application that enables fitting (e.g., self-fitting) and/or program adjustment of auditory prosthesis system 100 via external computing device 704.

External computing device 704 may be used, in some examples, to convey instructions for using auditory prosthesis system 100 to a user. For example, external computing device 704 may determine a configuration of auditory prosthesis system 100 (e.g., by receiving a dataset representative of the configuration from sound processor apparatus 104) and may identify instructions specific to the configuration that a user may access. Such instructions may, for example, identify which program of a plurality sound processing programs to select in various situations. Such an application may also enable a user to receive specific device use and diagnostic help. The application may, for example, allow a user to monitor working states of various components of auditory prosthesis system 100 using external computing device 704. For example, using external computing device 704, a user may confirm working states of auditory prosthesis system 100 components such as LED signal lights, program buttons, and/or volume buttons. The user may also check on implant lock/unlock status and perform microphone source testing via external computing device 704.

External computing device 704 may additionally include an operating room ("OR") mode that permits an individual with specified access privileges, such as a physician or other specialist, to conduct various system and/or patient response tests using external computing device 704 while various components of auditory prosthesis system 100 are being implanted within the patient. For example, while external computing device 704 is in OR mode, a physician may direct sound processor apparatus 104 to obtain various diagnostic measurements from cochlear implant 108 implanted within a patient, such as impedance measurements, neural response imaging measurements, and/or conditioning measurements. The diagnostic measurements may then be received by external computing device 704 from sound processor apparatus 104. External computing device 704 may additionally evaluate the received measurements (e.g., in conjunction with a second dataset acquired from a source other than sound processor apparatus 104). Based on this evaluation, external computing device 704 and/or a physician may change a sound processing program and/or make adjustments to one or more parameters of a sound processing program executed by sound processor apparatus 104.

Figure 11:
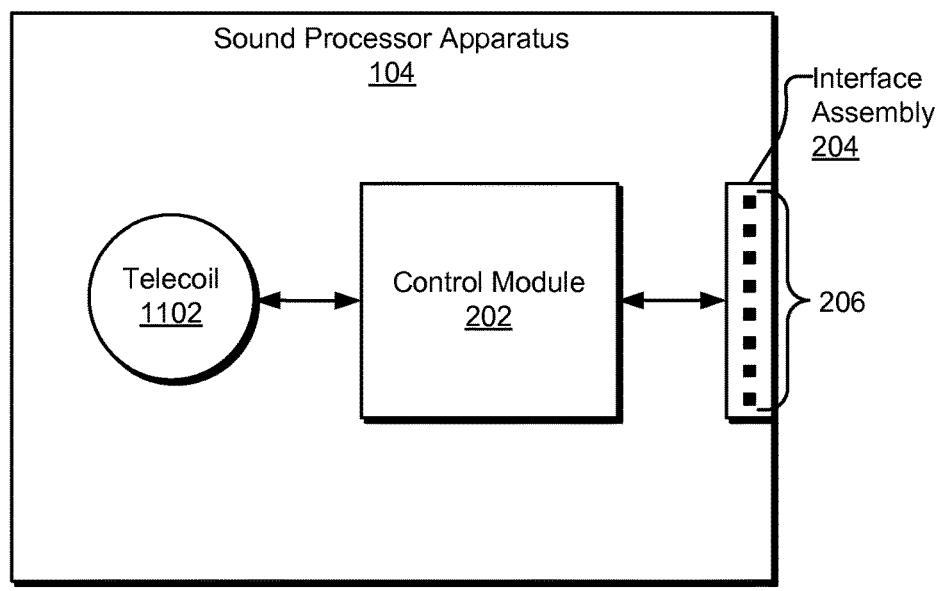
FIG. 11 illustrates exemplary components, including a telecoil, that may be included within a sound processor apparatus according to principles described herein.

FIG. 11 illustrates a sound processor apparatus 104 that includes a telecoil 1102. As shown, telecoil 1102 may be communicatively coupled to control module 202. Telecoil 1102 may be utilized in conjunction with a location (e.g., a building or room) that includes a telecoil loop for providing a direct audio feed from the telecoil loop to auditory prosthesis system 100 via telecoil 1102. In some embodiments, telecoil 1102 may be configured to receive a direct signal from another device, such as a telephone device equipped with telecoil communication capabilities.

Figure 12:
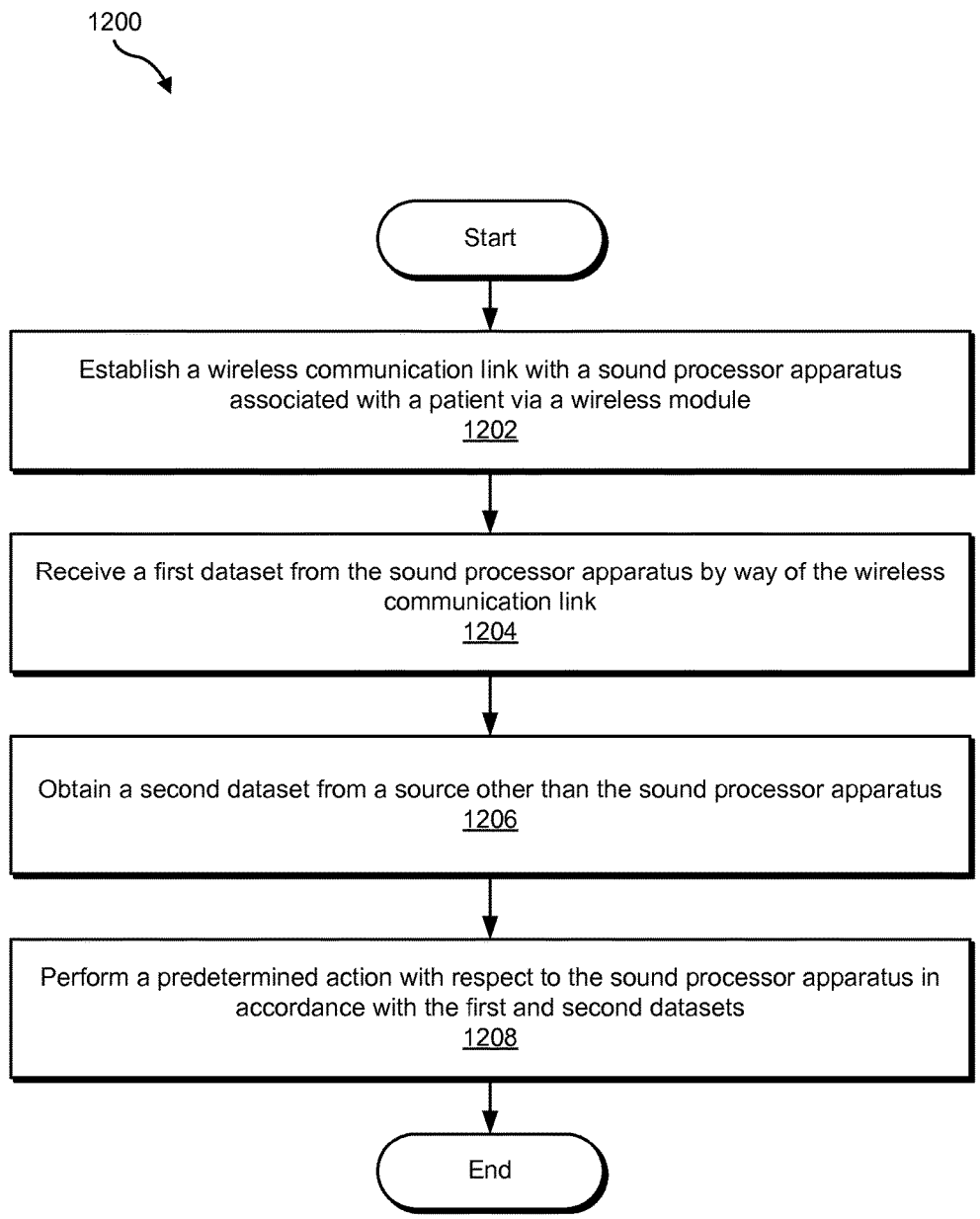
FIG. 12 illustrates an exemplary method according to principles described herein.

FIG. 12 illustrates an exemplary method 1200. While FIG. 12 illustrates exemplary steps according to one embodiment, other embodiments may omit, add to, reorder, and/or modify any of the steps shown in FIG. 12. One or more of the steps shown in FIG. 12 may be performed by external computing device 704 and/or any implementation thereof.

In step 1202, an external computing device establishes a wireless communication link with a sound processor apparatus associated with a patient via a wireless module. Step 1202 may be performed in any of the ways described herein.

In step 1204, the external computing device receives a first dataset from the sound processor apparatus by way of the wireless communication link. Step 1204 may be performed in any of the ways described herein.

In step 1206, the external computing device obtains a second dataset from a source other than the sound processor apparatus. Step 1206 may be performed in any of the ways described herein.

In step 1208 the external computing device performs a predetermined action with respect to the sound processor apparatus in accordance with the first and second datasets. Step 1208 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    an external computing device that:
        establishes a wireless communication link with a sound processor apparatus associated with a patient, wherein the sound processor apparatus is configured to be located external to the patient and control a cochlear implant configured to be implanted within the patient,
        receives a first dataset from the sound processor apparatus by way of the wireless communication link, the first dataset comprising data representative of one or more sound processing programs loaded onto the sound processor apparatus,
        obtains a second dataset from a source other than the sound processor apparatus, the second dataset comprising data associated with an environment of the external computing device,
        identifies, based on the first and second datasets, a sound processing program not already loaded onto the sound processor apparatus, and
        transmits, by way of the wireless communication link, data representative of the sound processing program to the sound processor apparatus.

2. The system of claim 1, wherein the second dataset is obtained by way of one or more measurements of the environment made by the external computing device.

3. The system of claim 1, wherein the second dataset is received from another computing device in communication with the external computing device.

4. The system of claim 1, wherein second dataset indicates at least one of:
    a physical location of at least one of the external computing device and the sound processor apparatus; and
    an environmental audio profile.

5. The system of claim 1, wherein the first dataset further comprises data representative of measurements obtained by the sound processor apparatus from cochlear implant circuitry implanted within the patient.

6. The system of claim 1, wherein the external computing device directs, based on the first and second datasets, the sound processor apparatus to change at least one of:
    a sound processing program executed by the sound processor apparatus, and
    a sound processing parameter utilized by the sound processor apparatus.

7. The system of claim 1, wherein the external computing device directs, based on the first and second datasets, the sound processor apparatus to enable or disable a functionality of the sound processor apparatus.

8. The system of claim 7, wherein the functionality comprises a telecoil functionality.

9. A method comprising:
    establishing, by an external computing device, a wireless communication link with a sound processor apparatus associated with a patient, the sound processor apparatus configured to be located external to the patient and control a cochlear implant configured to be implanted within the patient;
    receiving, by the external computing device, a first dataset from the sound processor apparatus by way of the wireless communication link, the first dataset comprising data representative of one or more sound processing programs loaded onto the sound processor apparatus;
    obtaining, by the external computing device, a second dataset from a source other than the sound processor apparatus, the second dataset comprising data associated with an environment of the external computing device;
    identifying, by the external computing device based on the first and second datasets, a sound processing program not already loaded onto the sound processor apparatus, and
    transmitting, by the external computing device by way of the wireless communication link, data representative of the sound processing program to the sound processor apparatus.

10. The method of claim 9, wherein the second dataset is obtained by way of one or more measurements of the environment made by the external computing device.

11. The method of claim 9, wherein the second dataset is received from another computing device in communication with the external computing device.

12. The method of claim 9, wherein second dataset indicates at least one of:
    a physical location of at least one of the external computing device and the sound processor apparatus; and
    an environmental audio profile.

13. The method of claim 9, wherein the first dataset further comprises data representative of measurements obtained by the sound processor apparatus from cochlear implant circuitry implanted within the patient.

14. The method of claim 9, further comprising directing, by the external computing device, the sound processor apparatus to change at least one of:
    a sound processing program executed by the sound processor apparatus, and
    a sound processing parameter utilized by the sound processor apparatus.

15. The method of claim 9, further comprising directing, by the external computing device, the sound processor apparatus to enable or disable a functionality of the sound processor apparatus.

16. The method of claim 15, wherein the functionality comprises a telecoil functionality.

* * * * *